US00PP09392P

United States Patent [19]

Crosby et al.

[11] Patent Number: Plant 9,392

[45] Date of Patent: Dec. 5, 1995

[54] APPLE TREE 'CO-OP 38'

[75] Inventors: Jeffrey A. Crosby, Louisiana, Mo.; Jules Janick, W. Lafayette; Edwin B. Williams, Lafayette, both of Ind.; Joseph Goffreda, Kendall Park, N.J.; Daniel F. Dayton, deceased, late of Urbana, Ill., by Grace M. Dayton, personal representative; Paul C. Pecknold, W. Lafayette, Ind.

[73] Assignee: Purdue Research Foundation, West Lafayette, Ind.

[21] Appl. No.: 70,988

[22] Filed: Jun. 2, 1993

[51] Int. Cl.[6] ..... A01H 5/00

[52] U.S. Cl. ..... Plt./35.1

[58] Field of Search ..... Plt./34.1, 35.1

*Primary Examiner*—James R. Feyrer

*Attorney, Agent, or Firm*—Woodard, Emhardt, Naughton, Moriarty & McNett

[57] ABSTRACT

The cultivar of the present invention, designated 'Co-op 38', is a new and distinct cultivar of apple tree (*Malus×domestica* Borkh.). It was discovered in October of 1980 at West Lafayette, Ind., in the course of an attempt to develop improved apple cultivars with high fruit quality and resistance to *Venturia inaequalis* (Cke.) Wint., the causal agent of the scab disease of apple. The tree is a seedling of known parentage planted in May of 1973 in the HE Block of the apple breeding orchard on the Hinsley tract of the Purdue Horticulture Research Farm, West Lafayette, Ind. In the above mentioned block, its position was Row 4, Tree 16, having the designation PRI 2750-6 in the breeding records.

2 Drawing Sheets

BACKGROUND OF THE INVENTION

The present new cultivar, 'Co-op 38', also known as 'Goldrush', was produced from crossing 'Golden Delicious' as the seed parent and the selection Co-op 17 (PRI 1661-1) as the pollen parent in 1972 at Urbana, Ill. The new cultivar carries the genetic factor $V_f$ inherited from *Malus floribunda* Sieb. 821 that renders it highly resistant to infection caused by *Venturia inaequalis*. For more than twenty years, trials of apple cultivars containing $V_f$ in every humid production area of the world have shown no breakdown of this resistance. The presence of this factor in 'Co-op 38' has been demonstrated by controlled greenhouse inoculation tests of the seedling and thirteen years of observation of the seedling and propagules under natural conditions for infection in the field at the West Lafayette site and at multiple sites in the U.S. and abroad for several years. The complete pedigree is shown in FIG. 3.

The new cultivar produces a moderately vigorous, slightly upright, spreading, sturdy branched, semi-spur tree, similar but slightly more upright and less vigorous than 'Golden Delicious'. Fruits have a tendency to be borne singly on short to moderate length spurs, on second and third year wood, and hang well on the tree. 'Co-op 38' is field immune to apple scab. Based on field observations it is moderately resistant to fire blight (incited by *Erwinia amylovora* (Burr.) Winslow), and has a high level of resistance to powdery mildew (incited by *Podosphaera leucotricha* (Ell. & Ev.) Salm.) It is susceptible to cedar-apple rust (incited by *Gymnosporagium juniperi-virgininae* (Schw.)).

Flowering occurs late in the bloom season, after 'Golden Delicious'. The fruit is best suited for use out of storage in winter and spring. The dessert quality is very good to excellent and reaches its peak in late winter and spring. Fruit retains characteristic quality (flavor and texture) for 7 months or more in refrigerated storage at 1° C.

After observations, the selection was asexually propagated by grafting on seedling, EMLA-111, and EMLA-7 rootstocks at the above noted Lafayette site. Preliminary observations indicate that grafted material has retained the described characteristics after propagation.

BRIEF DESCRIPTION OF THE FIGURES

The first figure is a photograph showing the leaves and fruit of 'Co-op 38'.

The second figure is a photograph showing the fruit of 'Co-op 38' on a larger scale.

Figure 1:
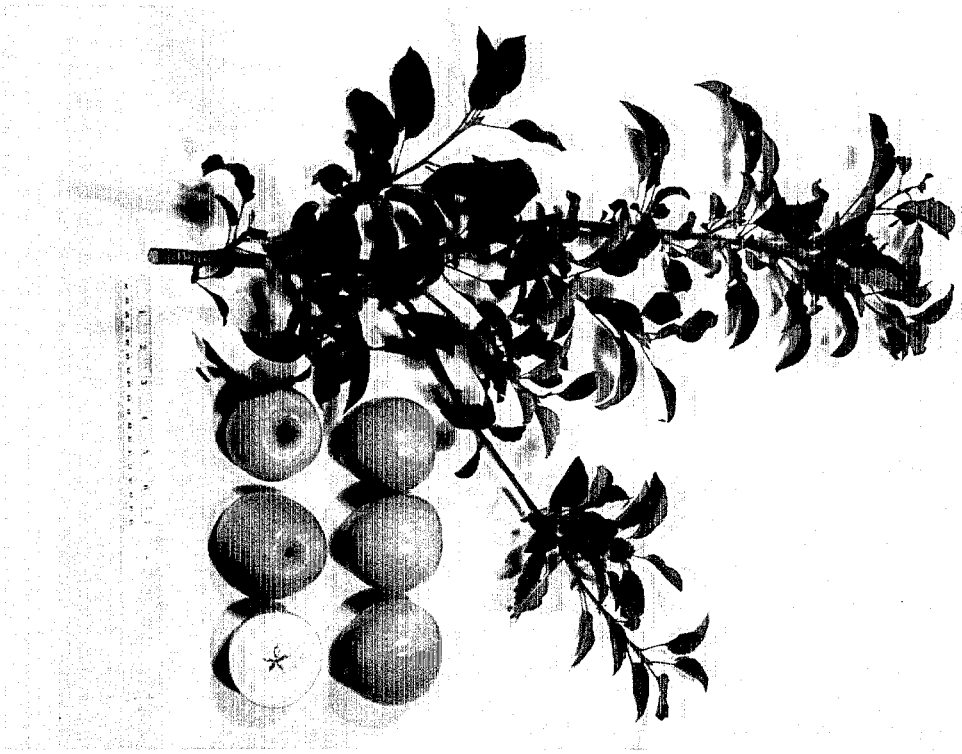
Figure 2:
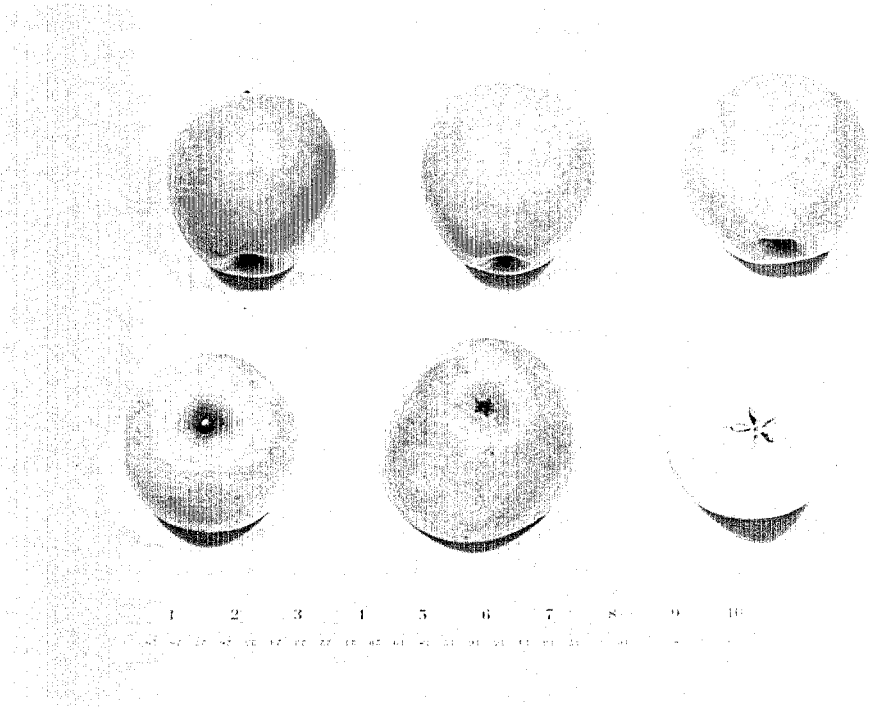
Figure 3:
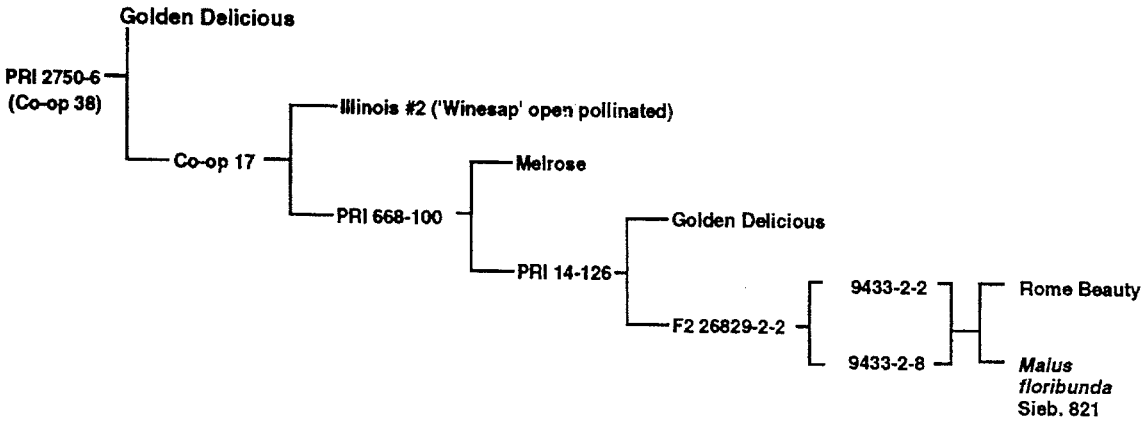

The third figure, entitled 'Pedigree', is a schematic diagram showing the pedigree of 'Co-op 38'.

DETAILED DESCRIPTION OF THE NEW CULTIVAR

The accompanying color photograph shows a typical example of fruit and foliage of 'Co-op 38'. The following is a detailed description of the new cultivar with color designations according to the 1966 Horticultural Colour Chart (Wilson) issued by The Royal Horticultural Society of London.

FLOWERS

Corolla: Average of 43 mm in diameter at anthesis.

Petals: 14 mm×21 mm.

Color: Rose Bengal; 25/1 to Magenta 27/1 (bud) fading to white margined or patterned with Rose Bengal 25/4 to Magenta 27/1 or lighter (open flowers). Adaxial surface of petals has more color and distinct patterns than abaxial surface. None of the petals are totally white, even at petal fall.

FRUIT

Shape: Ovate, regular.

*Length:width ratio.*—0.94.

Size: Average diameter is 70 to 76 mm.

Color: Greenish at harvest, developing 100% self-yellow color in storage from Lemon Yellow (Plate 4/1) to Saffron Yellow (Plate 7/2). Develops heavy blush on sun exposed side of fruit.

Skin: Smooth, non-waxy, tender, thin to medium in thickness; very conspicuous, russetted, round to stellate, scattered dots, not rough to the touch.

Stem: Medium to long, thin to medium.
Acute, medium depth, medium width, occasional russet.
Basin: Medium depth, medium breadth, sloping sides, regular surface.
Calyx: Persistent, open, erect to recurved.
Calyx tube: Conical.
Stamens: Median.
Core-lines: Clasping.
Core: Median, usually closed, medium sized.
Carpels: Round, emarginate, smooth.
Seeds: Full compliment, acute, non-tufted.
Flesh:

*Texture.*—Medium coarse grained, firm, very crisp and breaking.

*Quality.*—Very spicy and spritely acid at harvest; spicy, rich full flavor; very good to excellent quality which improves with moderation in acidity in storage; Brix at ripeness generally exceeds 12%.

*Color.*—Indian yellow (Plate 6/3).

Maturity season: October 20 to 30 at West Lafayette, Ind.; three weeks after 'Delicious'.
On-tree storage: Good on-tree storage characteristics with no tendency to develop water core.
Processing quality: Fruit has good processing quality.
Keeping quality: Very superior; quality improves in storage and is excellent in regards to both texture and flavor for at least 7 months at 1° C.
Use: Winter dessert apple, appropriate for medium and long term storage.

TREE

Tree: Slightly upright, moderately vigorous, limited branching, semi-spur bearing habit. Fruits are borne singly on short spurs and hang well on the tree even when over-ripe; some biennial tendency.
Leaves: Ovate to oval; serrate to double serrate margins; apex acute to acuminate, base acute to rounded; length to width ratio=1.87. Leaf petioles show anthocyanin pigmentation, which can be intense in tissues exposed to the sun.
Pruning training requirements: Tree has strong central leader with moderate growth; because of moderate growth minimal pruning and training will be required.
Branch angles: Commercially desireable branch angles, 70 to 90 degrees with little tendency for bark inclusion in crotch.
Pollination: Requires cross pollination for optimum yield.
Productivity: Moderately productive.
Thinning: Will require thinning to achieve optimum size.
Bark: Current year stems are Maroon (1030) on sun-exposed surface, Pea Green (61) on underside of new growth, lenticels on one-year-old wood are raised, about 1.0 to 1.3 mm in length, round to oblong, Apricot 609/3; lenticels on 5-year-old trunks are rough, slightly irregular, often circular, as large as 7×4 mm, typically 3 mm in length, Apricot 609/2.

We claim:

1. The new and distinct apple tree substantially as shown and described, characterized by resistance to apple scab, fire blight, and powdery mildew; extremely long storage life; attractive appearance; very good to excellent dessert quality which reaches its peak after storage; extremely crisp and breaking flesh texture; and maturity approximately three and one half weeks after 'Delicious' and six weeks after 'McIntosh'.

* * * * *

PEDIGREE

UNITED STATES PATENT AND TRADEMARK OFFICE

CERTIFICATE OF CORRECTION

PATENT NO. : PP09392

DATED : December 5, 1995

INVENTOR(S) : Jeffrey A. Crosby, Jules Janick, Edwin B.Williams, Joseph Goffreda, Daniel F. Dayton, Paul C. Pecknold , et al It is certified that error appears in the above-indentified patent and that said Letters Patent is hereby corrected as shown below:

In column 3, line 2, before "acute", please insert in lieu thereof --cavity:--.

In column 4, line 8, please insert a slash between "Pruning" and "training".

Signed and Sealed this

Sixteenth Day of April, 1996

Bruce Lehman

BRUCE LEHMAN

*Commissioner of Patents and Trademarks*

*Attest:*

*Attesting Officer*